(12) United States Patent
Cardoso et al.

(10) Patent No.: US 10,952,693 B2
(45) Date of Patent: Mar. 23, 2021

(54) SYSTEM AND METHOD TO MITIGATE X-RAY IMAGE PARALLAX BY TILTING THE SAMPLE

(71) Applicant: Creative Electron, Inc., San Marcos, CA (US)

(72) Inventors: Guilherme Cardoso, San Marcos, CA (US); Griffin Lemaster, Solana Beach, CA (US)

(73) Assignee: Creative Electron, Inc., San Marcos, CA (US)

( * ) Notice: Subject to any disclaimer, the term of this patent is extended or adjusted under 35 U.S.C. 154(b) by 0 days.

(21) Appl. No.: 16/703,774

(22) Filed: Dec. 4, 2019

(65) Prior Publication Data

US 2020/0305824 A1 Oct. 1, 2020

Related U.S. Application Data

(60) Provisional application No. 62/775,371, filed on Dec. 4, 2018.

(51) Int. Cl.
*G01N 23/04* (2018.01)
*A61B 6/00* (2006.01)

(52) U.S. Cl.
CPC .......... *A61B 6/5205* (2013.01); *A61B 6/4085* (2013.01)

(58) Field of Classification Search
CPC ........................... A61B 6/5205; A61B 6/4085
See application file for complete search history.

(56) References Cited

U.S. PATENT DOCUMENTS

| | | | |
|---|---|---|---|
| 6,198,798 B1 * | 3/2001 | Sauli | H01J 47/02 250/385.1 |
| 9,973,696 B1 * | 5/2018 | Meler | H04N 5/2624 |
| 2019/0199994 A1 * | 6/2019 | Hoglund | H04N 13/239 |

* cited by examiner

*Primary Examiner* — Kiho Kim

(57) ABSTRACT

A method for mitigating parallax for component reels being x-ray inspected, containing an x-ray inspection system and a plurality of reels circularly arranged in a conical field of view of an x-ray source of the x-ray inspection system, wherein a reels' inner edge is disposed higher than a reels' outer edge, wherein a plane of a reel is substantially parallel to a ray distances from the x-ray source.

1 Claim, 4 Drawing Sheets

X-ray Image of Reel with Components

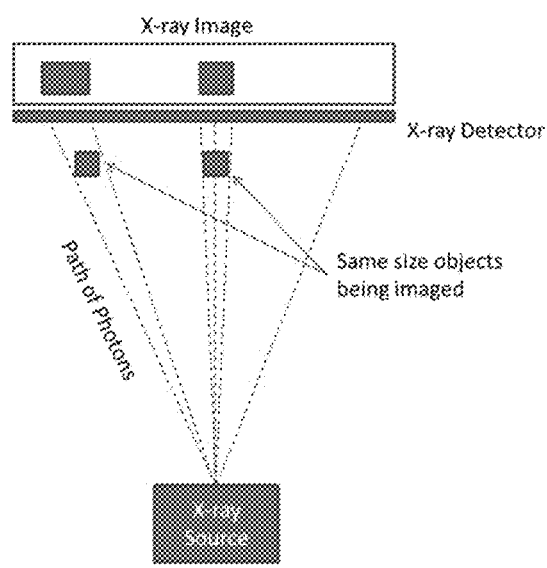
Figure 1: Explanation of Parallax

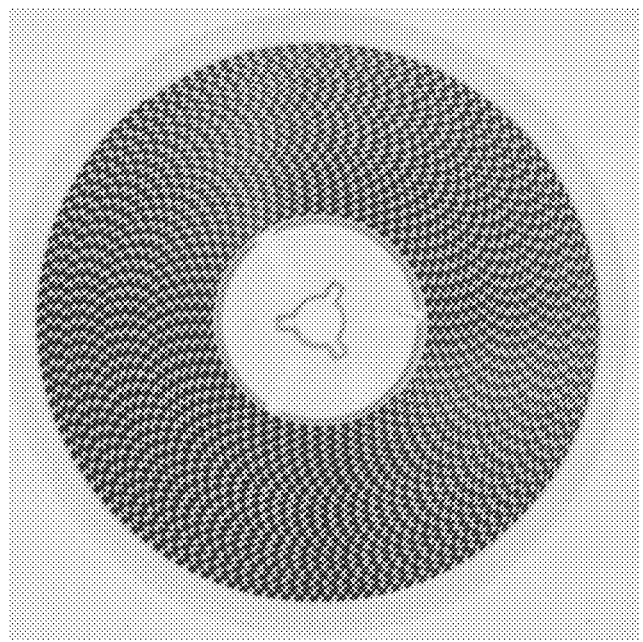
Figure 2: X-ray Image of Reel with Components

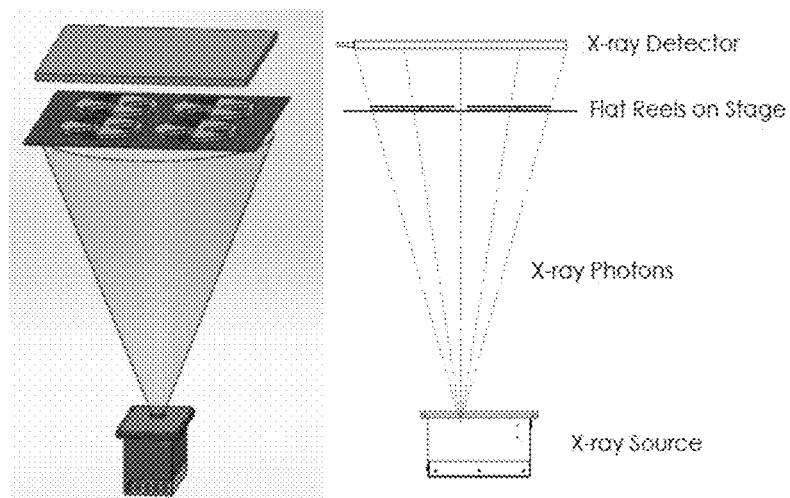
Figure 3: Prior art method for imaging multiple reels

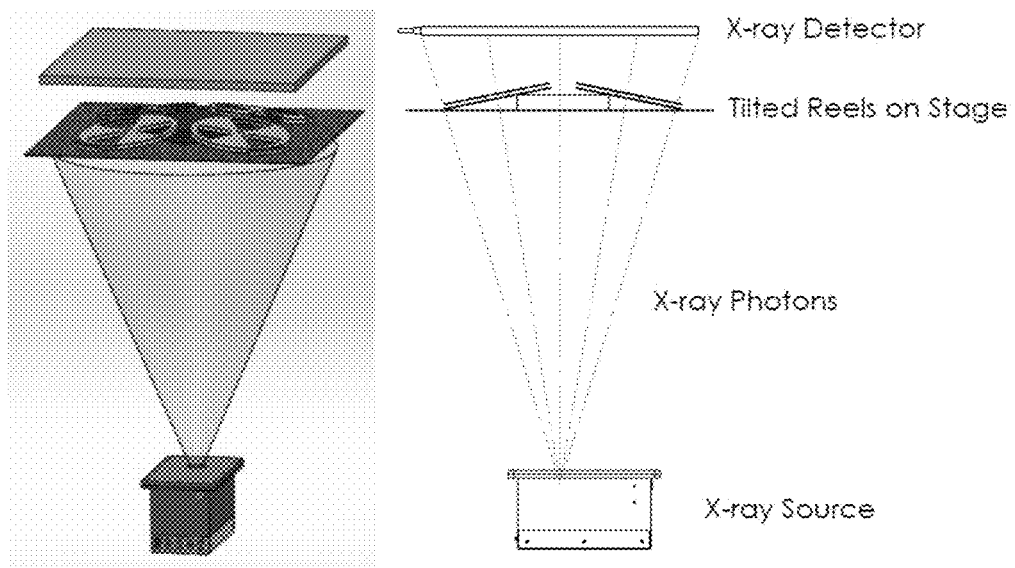
Figure 4: Method to Image Multiple Reels with Reduced Parallax

SYSTEM AND METHOD TO MITIGATE X-RAY IMAGE PARALLAX BY TILTING THE SAMPLE

CROSS-REFERENCE TO RELATED APPLICATION(S)

This application claims the benefit of U.S. Provisional Patent Application No. 62/775,371, filed Dec. 4, 2018, the contents of which is hereby incorporated by reference in its entirety.

FIELD

This invention relates to systems and methods for inspecting via x-ray analysis. More particularly, it is directed to mitigating parallax error by adjusting the sample's inclination.

BACKGROUND

When x-rays are generated using an electronic x-ray source, the x-ray photons emitted from the x-ray source are emitted in a conical pattern. When the photons reach an x-ray detector, the photons closer to the edge of the detectable area arrive at an angle, as opposed to normal to the surface. The effect on x-ray images is that anything not directly in the center of the x-ray cone, will have an elongated appearance stemming from the different angle of the arriving photons. This effect is called parallax and is an error condition.

Therefore, there has been a long-standing need in the industry for methods and systems for correcting parallax error. Details of one or more such approach(es) is provided in the below description.

SUMMARY

The following presents a simplified summary in order to provide a basic understanding of some aspects of the claimed subject matter. This summary is not an extensive overview and is not intended to identify key/critical elements or to delineate the scope of the claimed subject matter. Its purpose is to present some concepts in a simplified form as a prelude to the more detailed description that is presented later.

In one aspect of the disclosure, a method for mitigating parallax for component reels being x-ray inspected is provided, comprising, an x-ray inspection system; and a plurality of reels circularly arranged in a conical field of view of an x-ray source of the x-ray inspection system, wherein a reels' inner edge is disposed higher than a reels' outer edge, wherein a plane of a reel is substantially parallel to a ray distances from the x-ray source.

BRIEF DESCRIPTION OF THE DRAWINGS

FIG. 1 is an illustration showing parallax.
FIG. 2 is an x-ray image of a reel with components.
FIG. 3 contains illustrations showing a prior art method for imaging multiple reels.
FIG. 4 is an illustration showing an exemplary method to image multiple reels with reduced parallax.

DETAILED DESCRIPTION

FIG. 1 illustrates the parallax image in an x-ray inspection system, and is self-explanatory.

FIG. 2 shows an example of an x-ray image of a reel of components. Many components used in the electronics manufacturing industry are stored on reels, before being used in production. Taking an x-ray image of an entire reel, provides an image which can be run through algorithms to count the number of components present.

Components farther from the center exhibit more parallax than components closer to the center. Depending upon the size of the component and spacing within the reel, high parallax causes components to overlap one another. When placing a single reel in the center of the field of view, the parallax is evenly distributed as components are farther from the center. Image processing algorithms can be used to identify this trend and correctly count the components.

Problem

To improve throughput, multiple reels can be imaged, and processed at one time. The number of reels that can be imaged is limited by reel size and the field of view of the x-ray detector. This requires many, if not all, reels being imaged to be off center. When multiple reels of components are imaged in the orientation seen in FIG. 3, this results in high parallax on the parts farthest away from the center of the x-ray cone. The uneven distribution of parallax on each reel does not allow for the image processing algorithms to correctly identify individual components, and therefore count them incorrectly.

Proposed Solution

All reels are currently placed on a flat plane stage, parallel to the x-ray sensor, and normal to the center of the x-ray cone. As explained previously, this results in higher amounts of parallax the farther the feature is off center from the x-ray cone. In order to reduce the parallax seen on objects farther from the center of the x-ray cone, each reel will be placed at a new plane, normal to the x-ray cone at the center of their location. This results in each reel being tilted to an angle that is normal to the x-ray cone at the reel's center. This then creates a reduced and evenly distributed amount of parallax seen throughout the reel which can then be processed and counted using standard algorithms.

The new planes will be created by raising the center of the stage and creating braces on the outer edge of the reel location. When multiple reels are placed on the stage, they will then be tilted normal to the x-ray cone in their location as see in FIG. 4. Given the conical x-ray, the arrangement show in FIG. 4 addresses (or at least mitigates) the parallax error. The raising of the "inner" edge as compared to the "outer" edge of the reels can be easily accomplished with a center support that may or may not be conical in shape. An elevated disc, ring, segmented ring(s) may suffice. Any possible means for displacing the height of one edge of the reel to the opposite edge can be utilized. For example, instead of "raising", the outer edge may be "lowered".

Implicit in this discussion is the understanding that the x-ray system has a processor or computer that processes the captured x-ray images and applies the imaging algorithms. The processor or computer may be proximal or separate, depending on design preference.

The proposed solution is elegant and can be easily implemented. As should be apparent to one of ordinary skill in the art, various changes and modifications can be implemented without departing from the spirit and scope of this disclosure. As one non-limiting example, the tilting of the reels can be achieved by "hanging" them at an angle, that is, the reels may be suspended The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, implementations, and realizations, which can, of course, vary. It is also to be understood that the terminology used herein is for the purpose of describing particular embodiments only, and is not intended to be limiting.

What is claimed is:

1. A method for mitigating parallax for component reels being x-ray inspected, comprising:
    an x-ray inspection system; and
    a plurality of reels circularly arranged in a conical field of view of an x-ray source of the x-ray inspection system;
    wherein a reels' inner edge is disposed higher than a reels' outer edge, wherein a plane of a reel is substantially perpendicular to a ray distances from the x-ray source.

* * * * *